United States Patent [19]

Policello et al.

[11] Patent Number: 5,558,806
[45] Date of Patent: Sep. 24, 1996

[54] SURFACTANT BLEND OF A POLYALKLENEOXIDE POLYSILOXANE AND AN ORGANIC COMPOUND HAVING A SHORT CHAIN HYDROPHOBIC MOIETY

[75] Inventors: George A. Policello, Peekskill; Dennis S. Murphy, Brewster, both of N.Y.

[73] Assignee: OSI Specialties, Inc., Danbury, Conn.

[21] Appl. No.: 403,538

[22] Filed: Mar. 14, 1995

Related U.S. Application Data

[63] Continuation of Ser. No. 5,749, Jan. 19, 1993, abandoned, and a continuation-in-part of Ser. No. 917,846, Jul. 23, 1992, abandoned.

[51] Int. Cl.$^6$ .............. B01F 17/18; B01F 17/28; B01F 17/32; B01F 17/56
[52] U.S. Cl. ............. 252/355; 71/DIG. 1; 252/351; 252/353; 252/354; 252/356; 252/357; 504/116
[58] Field of Search .................. 252/351, 353, 252/354, 355, 356, 357, DIG. 7, 545; 71/DIG. 1; 548/543

[56] References Cited

U.S. PATENT DOCUMENTS

| | | |
|---|---|---|
| 2,052,027 | 8/1936 | Harris .................. 252/355 X |
| 2,129,264 | 9/1938 | Downing et al. .................. 554/103 |
| 2,247,266 | 6/1941 | Wibaut et al. .................. 252/355 X |
| 3,219,656 | 11/1965 | Boettner .................. 252/351 X |
| 3,299,112 | 1/1967 | Bailey .................. 556/445 |
| 3,562,786 | 2/1971 | Bailey et al. .................. 252/524 |
| 3,892,669 | 7/1975 | Rapisarda et al. .................. 252/545 X |
| 4,097,305 | 6/1978 | Chiesa, Jr. et al. .................. 252/DIG. 7 |
| 4,565,647 | 1/1986 | Llenado .................. 252/354 |
| 4,801,400 | 1/1989 | Login et al. .................. 252/357 |
| 5,104,647 | 6/1990 | Policello .................. 514/772 |
| 5,160,729 | 11/1992 | Login et al. .................. 548/543 X |

FOREIGN PATENT DOCUMENTS

| | | |
|---|---|---|
| 2080521 | 6/1993 | Canada . |
| 2080520 | 6/1993 | Canada . |
| WO891234 | 6/1989 | WIPO . |

OTHER PUBLICATIONS

Ananthapadmanabhan, E. P., et al., "A Study of the Solution, Interfacial and Wetting Properties of Silicone Surfactants," *Colloids and Surfaces*, 44 (1990) p. 281–297.

Balneaves, J. M., "Seasonal Effects of Glyphosate and Silwet M Applied to Mature Gorse," *Scrub, Forest Shelter*, Proc. 39th N. Z. Weed and Pest Control Conference, (1986), pp. 74–76.

Coggins, C. W. et al., "Possible Methods to Increase Efficacy of Gibberellic Acid Applied to Navel Orange Trees" Adjuvants and Agrichemicals, vol. 3, CRC Press (in press).

Field, R. J., et al., "Promotion of Stomatal Infiltration of Glyphosate by an Organosilicone Surfactant Reduces the Critical Rainfall Period," *Pestic*, Sci, 24, pp. 55–62 (1988).

Greenberg, J., et al., "Improving the Uptake of Gibberellic Acid ($GA_3$) by Citrus Fruit and Leaves," 1984 Proc. Plant Growth Regulator Soc. Amer., 11 pp. 16–25.

Motooka, P., et al., "Gorse Control with Herbicides and Its Enhancement with Surfactants," Proceedings 42nd Western Society for Weed Science, Conference (1989) pp. 161–166.

Murphy, G. J., et al., "Formulation Considerations For Trisiloxane Based Organosilicone Adjuvants," Brighton Crop Protection Conference—Weeds—1991 4A–8, pp. 355–362.

Zabkiewicz, J. A., et al., "Effect of Additives on Foliar Wetting and Uptake of Glyphosate into Gorse (*Ulex europaeus*)" (1985).

*Primary Examiner*—Richard D. Lovering
*Attorney, Agent, or Firm*—Andrew S. Reiskind

[57] ABSTRACT

A surfactant blend comprising a polyalkyleneoxide polysiloxane and an organic compound having a hydrophobic moiety containing less than 11 carbon atoms in the main chain or backbone and a method of using the surfactant blend as an adjuvant in pesticide sprays or crop oil concentrates.

11 Claims, No Drawings

SURFACTANT BLEND OF A POLYALKLENEOXIDE POLYSILOXANE AND AN ORGANIC COMPOUND HAVING A SHORT CHAIN HYDROPHOBIC MOIETY

This application is a continuation of Ser. No. 08/005,749 filed Jan. 19, 1993, now abandoned, and is a continuation-in-part of Ser. No. 07/917,846, filed Jul. 23, 1992, now abandoned.

BACKGROUND OF THE INVENTION

1. Field of the Invention

The present invention relates to a surfactant blend useful as an adjuvant for dispersing, wetting, and spreading pesticides and a method for enhancing the efficacy of a pesticide. More particularly, the present invention relates to a surfactant blend containing a polyalkyleneoxide polysiloxane and an organic compound containing a short chain (less than 11 carbon atoms in the main chain or backbone) hydrophobic moiety and a hydrophilic moiety. This invention also relates to a method of using the surfactant blend to enhance the efficacy of pesticides.

2. Prior Art

Surfactant formulations are commonly used in forestry, agriculture, and horticulture as agricultural adjuvants to improve the efficacy of pesticides such as micronutrients, biologicals, herbicides, fungicides and growth regulators. Surfactants are often used as dispersants, wetting and spreading agents, and emulsifiers in a formulated product or package or in a tank mix.

Organosilicone surfactants provide surface tension values significantly lower than other commonly used surfactants (21 mN/m v. 30 mN/m, respectively). For example, the use of an organosilicone surfactant such as SILWET® L-77 OSI Specialties, Inc. in combination with a pesticide results in increased foliar uptake of the pesticide and, hence, increased efficacy of the pesticide in control of weed growth.

However, in aqueous mixtures of organosilicones with conventional organic surfactants, such as nonyl phenol ethoxylates, the organic surfactant components are known to interfere with the spreading performance of the organosilicones. While it has been previously shown in U.S. Pat. No. 5,104,647 that polyalkylene oxide copolymers, such as PLURONIC® copolymers, when blended with organosilicone surfactants do not interfere with their aqueous spreading capability, these blends have limited ability to effectively emulsify water-insoluble agricultural products such as pesticides, crop oils and the like and limited ability to adequately reduce aqueous surface tension.

Accordingly, there is a need for a surfactant blend which has acceptable spreading in aqueous solutions while effectively emulsifying water-insoluble agricultural products. That is, there is a need for a surfactant blend having a high degree of surface activity as measured by the ability to reduce surface tension and the ability to form micelles which are important factors in emulsifying, spreading, and wetting. By "micelle" is meant an aggregated structure of surfactant monomers. Micelles form in the aqueous mixture at the critical micelle concentration which is evidenced by a sharp break in the surface tension versus concentration curve.

SUMMARY OF THE INVENTION

The present invention provides a surfactant blend comprising a polyalkyleneoxide polysiloxane and an organic compound having a hydrophobic moiety containing less than 11 carbon atoms and a hydrophilic moiety that is nonionic, anionic, cationic or zwitterionic. This surfactant blend of the present invention provides for the acceptable dispersion of pesticide actives without significantly interfering with spreading capability of the organosilicone component in aqueous solutions. The surfactant blend is especially useful in agricultural applications as an adjuvant to improve the efficacy and delivery of pesticides such as micronutrients, biologicals, herbicides, fungicides and growth regulators, and can more effectively emulsify water-insoluble agricultural products.

DETAILED DESCRIPTION OF THE INVENTION

The surfactant blend of the present invention comprises a polyalkyleneoxide polysiloxane and an organic compound containing a short chain (less than 11 carbon atoms in the main chain or backbone) hydrophobic moiety and a hydrophilic moiety.

Polyalkyleneoxide Polysiloxane

The polyalkyleneoxide polysiloxane employed in the surfactant blend of the present invention is more particularly defined by the general formula:

(I)

In Formula I, x has a value of 1 to 2 and preferably x is 1. As set forth in Formula I, $R^1$ has the formula:

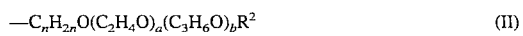
(II)

where n has a value of 3 or 4, preferably n is 3;

a has a value of 1 to 15, preferably a is 6 to 9;

b has a value of 0 to 14, preferably b is 0 to 3; and most preferably b is 0;

a+b has a value of 5 to 15, preferably 6 to 9 and each $R^2$ is the same or different and is selected from the group consisting of hydrogen, an alkyl having 1 to 4 carbon atoms, and an acetyl group.

The molecular weight of the oxyalkylene group (Formula II) is less than or equal to 1000. Preferably, the molecular weight of the oxyalkylene group is less than or equal to about 600, and most preferably ranges from about 300 to 500. Thus, the values of a and b can be those numbers which provide molecular weights within these ranges. However, the number of oxyethylene units ($—C_2H_4O$) in the polyether chain (Formula II) must be sufficient to render the polyalkyleneoxide polysiloxane water dispersible or water soluble. It is understood that when b is a positive number, the oxyethylene and oxypropylene units ($—C_3H_6O$) may be distributed randomly throughout the polysiloxane chain or in respective blocks of oxyethylene and oxypropylene units or a combination of random and block distributions.

The preparation of polyalkyleneoxide polysiloxanes is well known in the art. Polyalkyleneoxide polysiloxanes of the present invention may be prepared according the procedure set forth in U.S. Pat. No. 3,299,112. Typically, polyalkyleneoxide polysiloxanes of the surfactant blend of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy endblocked polyalkylene oxide). The reaction conditions employed in addition reactions of this type are well known in the art and in general involve heating the reactants (e.g., at temperature of from about 85° C. to 110° C.) in the presence of a platinum catalyst (e.g., chloroplatinic acid) and a solvent (e.g., toluene).

Organic Compound

In addition to the polyalkyleneoxide polysiloxane, the surfactant blend of the present invention contains an organic compound containing a short chain (less than 11 carbon atoms in the main chain or backbone) hydrophobic moiety, $$CH_3(CH_2)_c(\underset{R^3}{\overset{R^3}{C}})_d-$$

and a hydrophilic moiety, $-O_tR^4$. The organic compound of the surfactant blend of the present invention, preferably contains a short chain hydrophobic moiety having 6 to 10 carbon atoms in the main chain or backbone, and can also contain branched structures such as trimethylnonal, dimethylhexyl, and the like. The hydrophilic moiety of the organic compound of the surfactant blend of the present invention can be nonionic, anionic, cationic or zwitterionic. More particularly, the organic compound of the surfactant blend has the general formula:

$$\left[CH_3(CH_2)_c(\underset{R^3}{\overset{R^3}{C}})_dO_t\right]_y R^4 \quad (III)$$

wherein $R^3$ is the same or different and is selected from the group consisting of hydrogen and an alkyl group having 1 to 4 carbon atoms.

When the hydrophilic moiety of the organic compound is a nonionic group, it can be, for example, polyalkyleneoxide, a pyrrolidone, and mono- and polyglucosides. The polyalkyleneoxide can be selected from the group consisting of polyethyleneoxide, random or block copolymers of ethylene oxide and propylene oxide, and mixtures thereof, such that the resulting surfactant blend is water dispersible or water soluble.

Examples of nonionic surfactants suitable for the surfactant blend of the present invention can include, octyl alcohol ethoxylates such as DEHYDOL® 04 (Henkel Corporation, Ambler, Pa.), decyl alcohol ethoxylates, such as EMULPHOGENE® DA-530 (Rhone-Poulenc, Cranbury, N.J.), trimethylnonanol ethoxylates, such as TERGITOL® TMN-6 (Union Carbide Chemicals and Plastics Company Inc., Danbury, Conn.) and alkylpolyglucosides, such as TRITON® CG-100 (Union Carbide Chemicals and Plastics Company Inc.).

More particularly, in Formula III, when the hydrophilic moiety of the organic compound is a nonionic group, the hydrophobic moiety is defined by y is 1;

c has a value of 5 to 9, preferably 5 to 7;

d has a value of 0 to 4, preferably 0 to 3;

c+d has a value of 5 to 9, preferably 7 to 9; and
the hydrophilic moiety is defined by t having a value of 0 or 1;

when t is 1,
$R^4$ is selected from the group consisting of
(i)-$[C_2H_4O]_f[C_3H_6O]_gH$ and (ii)-$(C_6H_9O_5)_h$—$C_6H_{10}O_5$; and
when t is 0,
$R^4$ is (iii) $-N\overset{\overset{O}{\|}}{\underset{\diagdown}{\diagup}}$ ;

wherein f has a value of 1 to 40, preferably
f is 2 to 15;

g has a value of 0 to 40, preferably
g is 0 to 10, most preferably g is 0; and h has a value of 1 to 4.

When the hydrophilic moiety of the organic compound is an anionic group, it can be, for example, a sulfonate, sulfate, ethoxy sulfate, phosphate ester, or a carboxylate wherein the counterion ($M^+$) is, for example, sodium, potassium, lithium, ammonium, diethanolammonium, or triethanolammonium. Examples of organic compounds having anionic moieties that are employed in the surfactant blend of the present invention are sodium 2-ethylhexyl sulfate, sodium n-decyl sulfate, sold under the trade name AVIROL® SA 4106 (Henkel Corporation, Ambler, Pa.), and dihexylsulfosuccinate, sold under the trade name AEROSOL® MA-80 (American Cyanamid, Wayne, N.J.).

More particularly, in Formula III, when the hydrophilic moiety of the organic compound is an anionic group, the hydrophobic moiety is defined by y is 1 or 2;

when y is 1, c has a value of 5 to 9, preferably 7 to 9;

d has a value of 0 to 4, preferably 0 to 3;

c+d has a value of 5 to 9, preferably 7 to 9; and
the hydrophobic moiety is defined by t having a value of 0 or 1;

when t is 1, $R^4$ is selected from the group consisting of
(i)-$[C_2H_4O]_qSO_3^-M^+$ wherein g is 1 to 3; and
(ii)-$SO_3^-M^+$;

when t is 0 then $R^4$ is $SO_3^-M^+$ when y is 2, c is 3 to 5, preferably 5;

d is 0 to 2, preferably 0;

c+d is 4 or 5, preferably 5;

when t is 1, then
$R^4$ is $$-\underset{\|}{\overset{O}{C}}-\underset{\|}{\overset{SO_3^-M^+}{CH}}-CH_2-\underset{\|}{\overset{O}{C}}-;$$

and
$M^+$ is selected from the group consisting of $Na^+$, $Li^+$, $K^+$, $N(CH_3)_4^+$, and $[C_2H_4OH]_3NH^+$.

When the hydrophilic moiety of the organic compound is a cationic group, the cationic group is, for example, selected from the group consisting of a protonated tertiary amine, a quaternary ammonium, a quaternary imidizolinium, pyridinium, and mixtures thereof wherein the counterion ($X^-$) is, for example, acetate, chloride, or bromide. An example of an organic compound having a cationic moiety employed in the surfactant blend of the present invention is dimethyl octyl ammonium acetate. Dimethyl octyl ammonium acetate is prepared by adding a stoichiometric amount of glacial acetic acid to dimethyloctylamine and diluting with water to the desired concentration.

More particularly, in Formula III when the hydrophilic moiety of the organic compound is a cationic group, the hydrophobic moiety is defined by y is 1 c has a value of 5 to 9, preferably 7 to 9;

d has a value of 0 to 4, preferably 0 to 3;

c+d has a value of 5 to 9, preferably 7 to 9; and
the hydrophibic moiety is defined by t is 0, and $R^4$ is selected from the group consisting of

 (i)

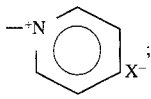 (ii)

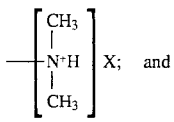 (iii)

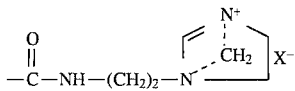 (iv)

wherein $X^-$ is selected from the group consisting of $Cl^-$, $Br^-$, $I^-$, $SO_4^-$, $HPO_4^-$, and $CH_3COO^-$.

When the hydrophilic moiety of the organic compound is a zwitterionic group, it can be, for example, a caprylampho carboxy glycinate (Mackam® 2CYSF from the Mcintyre Group, University Park, Ill.).

More particularly, in Formula III, when the hydrophilic moiety of the organic compound is a zwitterionic group, the hydrophobic moiety is defined by y is 1 c has a value of 5 to 9, preferably 5 to 7;

d has a value of 0 to 4, preferably 0 to 3;

c+d has a value of 5 to 9, preferably 7 to 9; and the hydrophilic moiety is defined by t is 0; and $R^4$ is selected from the group consisting of

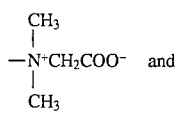 (i)

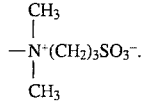 (ii)

Preparation of the Surfactant Blend

The surfactant blend of the present invention is prepared by combining the polyalkyleneoxide polysiloxane and the organic compound. The order of addition of the polysiloxane and organic compound is not critical, and, hence, they can be charged in any order to a vessel and mixed by stirring, shaking, or by any other means known to those skilled in the art. The two components can be mixed neat or blended as a solution, dispersion or emulsion. Preferably a homogeneous mixture is formed. The solution, dispersion, or emulsion of the components can be aqueous or non-aqueous. If a non-aqueous solution, dispersion, or emulsion is desired, the polysiloxane and organic compound may be placed in a nonaqueous solvent such as, for example, isopropanol and glycol ethers or in any liquid in which they are miscible.

In general, the weight ratio of the polyalkyleneoxide polysiloxane to the organic compound is not critical and ranges from about 1:99 to 99:1, preferably from about 2:8 to 8:2, and most preferably from about 3:7 to 7:3. When other additives such as a solvent, for example, are employed in the blend, such additives are usually present in amounts up to about 20% by weight of the blend, typically up to about 10% by weight of the blend.

The surfactant blends of the present invention find particular utility as adjuvants for dispersing, wetting and spreading pesticides. In particular these surfactant blends have been found to improve the spreading properties of aqueous dispersions or emulsions of commonly used agricultural products, such as crop oil concentrates and emulsifiable concentrates. The surfactant blend of this invention can be employed as part of the formulation of the agricultural product or can be added separately to the tank mix. In addition, these surfactant blends have been found to assist the efficacy of pesticides.

The surfactant blends of the present invention improve the spreading of foliar applied pesticidal sprays. Illustrative pesticides which can be employed in the present invention include those from the groups consisting of growth regulators, photosynthesis inhibitors, mitotic disruptors, lipid biosynthesis inhibitors, cell wall inhibitors, and cell membrane disruptors.

Growth regulators:

Phenoxy Acetic Acids, such as 2-4-D [(2,4-Dichlorophenoxy)acetic acid]

Phenoxy Propionic Acids, such as

Dichlorprop

[(RS)-2-(2,4-dichlorophenoxy)propionic acid]

Mecoprop [(RS)-2-(4-chloro-o-tolyloxy) propionic acid]

Phenoxy Butyric Acids, such as 2,4-DB [4-(2,4-Dichlorophenoxy)butyric acid]

Benzoic Acids, such as

Dicamba [3.6-dichloro-o-anisic acid]

Other growth regulators, such as

Fluoroxypyr

[4-amino-3,5-dichloro-6-fluoro-2-pyridloxyacetic acid]

Picloram [4-amino-2,3,5-trichloro-2-carboxylic acid]

Triclopyr [3,5,6-trichloro-2-pyridyloxyacetic acid]

Copyralid [3,6-dichloropyridine-2-carboxylic acid]

Photosynthesis inhibitors:

Triazines and s-Triazines such as

Hexazinone [3-cyclohexyl-6-dimethylamino-1-methyl- 1,3, 5-triazine-2,4(1H,3H)-dione]

Metribuzin [4-amino-6-tert-butyl-3-methylthio-1,2,3-triazine- 5(4H)-one]

Atrazine [6-chloro-N2-ethyl-N4-isopropyl]-1,3,5-triazine-2,4-diamine]

Simazine [6-chloro-$N^2$,$N^4$-diethyl-1,3,5-triazine-2,4-diamine]

Cyanazine 2-[4-chloro-6-(ethylamino)-1,3,5-triazin- 2-yl] amino]-2-methylpropanenitrile Prometon [$N^2$,$N^2$4-di-isopropyl-6-methoxy-1,3,5-triazine-2,4,diamine]

Ametryn [$N^2$-ethyl-$N^2$-isopropyl-6-methylthio-1,3,5-triazine- 2,4-diamine]

Substituted ureas, such as

Diuron [3-(3,4-dichlorophenyl)-1,1-dimethylurea(I)]

Fluometuron [1,1-dimethyl-3-(a,a,a,-trifluoro-m-tolyl)urea(I)]

Linuron [3-(3,4-dichlorophenyl)-1-methoxy-1-methylurea (I)]

Tebuthiuron [1- (5-tert-butyl, 1,3,4-thiadiazol-1-yl)-1,3-dimethylurea(I)]

Uracils, such as

Bromacil [5-bromo-3-sec-butyl-6-methylureacil (I)]

Terbacil [3-tert-butyl-5-chloro-6-methyluracil (I)]
Other photosynthesis inhibitors, such as
Bentazon [3-isopropyl-1H-2,1,3-benzothiadazin-4(3H)-one 2,2-dioxide (I)]
Desmedipham [ethyl 3'-phenylcarbamoyloxycarbanilate; ethyl 3-phenylcarbamoyloxypenylcarbamate; 3-ethoxycarbonylaminophenyl phenylcarbamate.]
Methazole [2-(3,4-dichlorophenyl)-4-methyl-1,2,4-oxadiazolidine- 3,5-dione(I)]
Phenmedipham [methyl 3-(3-methylcarbaniloyloxy) carbanilate; 3-methoxycarbonylaminophenyl 3'-methylcarbanilate.]
Propanil [3',4'-dichloropropionanilide (I)]
Pyridate [6-chloro-3-phenylpyridazine-4-yl S-octyl thiocarbonate]
Pigment Inhibitors: such as
Amitrole, [1H-1,2,4-triazol- 3-ylamine; 3-amino-1H-1,2,4-triazole]
Clomazone [2-(2-chlorobenzyl)-4,4-dimethyl-1,2-oxazolidin- 3-one; 2-(2-chlorobenzyl)-4,4-dimethylisoxazolidin-3-one]
Fluridone [1-methyl-3-phenyl-5-(a,a,a-trifluoro-m-tolyl)-4-pyridone]
Norflurazone [4-chloro-5-methylamino-2-(a,a,a-trifluoro-m-tolyl)pyridazine- 3(2H)-one]
Mitotic disruptors: Dinitroanilines, such as
Isopropalin [4-isopropyl-2,6-dinitro-N,N-dipropylaniline]
Oryzalin [3,5-dinitro-N,N-dipropylsulfanilamine (I)]
Pendimethalin [N-(1-ethylpropyl)-2,6-dinitro-3,4-xylidine]
Prodiamine [5 -dipropylamino-a,a,a-trifluoro-4-6-dintro-o-toluidine;
2,6-dinitro-$N^1$,$N^1$-dipropyl-4-trifluormethyl-m-phenylenediamine]
Trifluralin [a,a,a-trifluoro-2,6-dinitro-N,N-dipropyl-p-toluidine (I)]
Inhibitors of amino acid synthesis, such as
Glyphosate [N-(phosphonomethyl)glycine(I)]
Sulfonylureas, such as
Bensulfuron [a-(4,6-dimethoxypyrimidin-2-ylcarbamoylsulfamoyl)-o-toluic acid]
Chlorimuron [2-(4-chloro-6-methoxypyrimidin-2-ylcarbamoylsulfamoyl)benzoic acid]
Chlorsulfuron [1-(2-chlorophylsulfonyl)-3-(4-methoxy-6-methyl-1,3,5-triazin-2-yl)urea]
Metsulfuron [2-(4-methoxy-5-methyl-1,3,5-triazin-2-ylcarbamoylsulfamoyl)benzoic acid]
Nicosulfuron [2-(4,6-dimethoxypyrimidin-2-ylcarbamoylsulfamoyl)-N,N-dimethyl-nicotinamide; 1-(4,6-dimethoxy-pyrimidin-yl)-3-(3-dimethylcarbamoyl-2-pyridylsulfonyl)urea]
Primisulfuron [2-[4-6-bis(difluoromethoxy)pyrimidin- 2-ylcarbamoylsulfamoyl]benzoic acid]
Sulfometuron [2,(4,6-dimethylpyrimidin-2ylcarbamoylsulfamoyl)benzoic acid;
2-[3-(4,6-dimethylpyrimidin-2yl)ureidosulfonyl]benzoic acid]
Thifensulfuron [3-(4-methoxy-5-methyl-1,3,5-triazine-2-ylcarbamoylsulfamoyl)thiophen-2-carboxylic acid]
Trisulfuron [1-[2-(2-chloroethoxy)phenylsulfonyl]- 3(4-methoxy-6-methyl-1,3,5-triazin-2yl)urea]
Tribenuron [2-[4-methoxy-6-methyl-1,3,5-triazin- 2yl(methyl)carbamoylsulfamoyl]benzoic acid]
Imidazolinone, such as
Imazamethabenz [a reaction product comprising
(±)-6-(4-isopropyl-4-methyl-5-oxo-2-imadazolin 2-yl)-m-toluic acid (i) and
(±)-2-(4-isopropyl-4-methyl-5-oxo-2-imidazolin- 2-yl)-p-toluic acid (ii)]
Imazapyr [2-(4-isopropyl-4-methyl-5-oxo-2-imidazolin-2-yl)nicotinic acid]
Imazaquin [(RS)-2-(4-isopropyl-4-methyl-5-oxo-2-imadazolin- 2-yl)quinoline-3-carboxylic acid]
Imazethapyr [(RS)-5-ethyl-2-(4-isopropyl-4-methyl-5-oxo-2-imidazolin-2-yl)nicotinic acid]
Inhibitors of lipid biosynthesis, such as
Clethodim [(±)-2-[(E)-3-chloroallyloxyimino]propyl]- 5[2-(ethylthio)propyl]-3-hydroxycyclohex-3-enone]
Diclofop-methyl [(RS)-2-[4-(2,4-dichlorophenoxy) phenoxy]propionic acid]
Fenoxaprop-ethyl [±-2-[4-(6-chloro-1,3-benzoxazol-2-yloxy)phenoxy]propionic acid; (±)-2-[4-(5-chlorobenzoxazol-2-yloxy)phenoxy]propionic acid]
Fluazifop-P-butyl [(R)-2-[4-(5-trifluromethyl-2-pyridlyoxy)phenoxy]propionic acid]
Haloxyfop-methyl [(RS)-2-[4-(3-chloro-5-trifluoromethyl-2-pyridyloxy)phenoxy]propionic acid]
Quizalofop [(RS)-2[4-(6-chloroquinoxalin-2-yloxy) phenoxy]propionic acid]
Sethoxydim [(±)-(EZ}-2-(1-ethoxyiminobutyl)-5-[2-(ethylthio)propyl]- 3-hydroxycyclohex-2-enone]
Cell well inhibitors, such as
Dichlobenil [2,6-dichlorobenzonitrile(I)]
Isoxaben [N-[3-(1-ethyl-1-methylpropyl)-1,2-oxazol-5-yl]-2,6-dimethoxybenzamide;
N-[3-(1-ethyl-1-methylpropyl)isoxazol-5-yl]-2,6-dimethoxybenzamide]
Cell membrane disruptors: Bipyridylium compounds, such as
Diquat [9,10-dihydro-8a-diazoniaphenanthrene;
6-7-dihydrodipyridol[1,2-a:2',1'-c]pyrazine- 5,8-di-ium;
1,1'-ethylene-2,2'-bipyridyldiylium]
Paraquat [1,1'-dimethyl-4,4'bipyridinium(I)]
Diphenylethers, such as
Acifluorfen [5-(2-chloro-a,a,a-trifluro-p-tolyoxy)-2-nitrobenzoic acid]
Fomesafen [5-(2-chloro-a,a,a-trifluro-p-tolyloxy)-N-mesyl-2-nitrogenzamide; 5-(2-chloro-a,a,a-trifluoro- p-tolyoxy)-N-methylsulfonyl- 2-nitrobenamide], commercially available as REFLEX®
Lactofen [ethyl 0-[5-(2-chloro-a,a,a,-trifluoro-p-tolyloxy)-2-nitrobenzoyl]-DL-lactate]
Oxyfluorfen [2-chloro-a,a,a-trifluoro-o-tolyl 3-ethoxy-4-nitrophenyl ether]
Other herbicides:
Glufosinate [4-[hydroxy(methyl)phosphinoyl]-DL-homalanine;
DL-homoalanin-4-yl(methyl)phosphinic acid]
Bromoxynil, [3,5-dibromo-4-hydroxybenzonitrile(I)]; 3,5-dibromo-4-hydroxyphenyl cyanide; for ester, 2,6-dibromo-4-cyanophenyl octanoate(II)]

The above pesticides are intended merely as representative of the types of pesticides which can be employed with the surfactant blend of the present invention.

Pesticide compositions suitable for use with the surfactant blend of the present invention include both package and tank mix compositions. A pesticide composition will commonly contain an active ingredient or pesticide, a wetting agent such as a surfactant and a solvent such as water. Optionally, an oil such as conventional crop oil, can also be included as a solvent for emulsion concentrates. The surfactant blend of the present invention is incorporated into a pesticide composition at a concentration that will deliver enough surfactant blend to promote wetting. Generally, the amount of surfactant blend will be sufficient to deliver at least 0.02% volume/volume in the pesticide composition as applied.

Preferably, the amount of surfactant blend employed in the pesticide composition as applied ranges from about 0.025% to about 0.5% volume/volume.

Pesticide Composition Preparation

The components employed in the pesticide composition can be combined in any order. For example, the composition can be prepared by starting with a pesticide and adding the various components in any order. For example, the surfactant blend can be added to the pesticide or the ingredients comprising the surfactant blend can be added individually in any order to the pesticide. Water can be employed, if desired, in any amount desired.

While the ratios of concentrations of the various components of the pesticide composition of the present invention are herein suggested, those of skill in the art will recognize that minor variations may be necessary to accommodate particular characteristics of acceptable pesticides which can be employed in this invention.

Typically for a pesticide composition of the present invention, the concentration of pesticide active ingredient will be in the range from about 2 to about 75% by weight and preferably in the range from about 4 to about 40% by weight based upon the total composition.

In a final application solution of the pesticide composition of the present invention as, for example, in a spray solution applied to foliage, the concentration of pesticide active ingredient will be in the range from about 0.0001% to about 20% by weight, preferably in the range from about 0.05% to about 10% by weight, and most preferably 0.1% to 5% by weight of a final application solution.

The ratio of pesticidally active ingredient to the surfactant blend will be about the same whether the composition is a concentrate or a spray. Typically, the weight ratio of active ingredient of the pesticide to the surfactant blend is from about 1:99 to about 99:1 and preferably is in the range from about 40:60 to about 60:40.

The amount of water which is employed to prepare the concentrate or final application concentration, as in a spray, is adjusted as necessary. The concentrate and/or final composition may be a dry formulation.

Those of skill in the art will recognize that some departures may be made in the above ranges without significantly affecting the performance of the composition of this invention.

The ratio of pesticide active ingredient to adjuvant such as in a tank mix is not critical and will depend a great deal upon the nature and type of the pesticide active ingredient which is present in the composition. However, typically, the weight ratio of pesticide active ingredient to surfactant blend (adjuvant) is in the range from about 1:5 to about 10:1 and preferably is in the range from about 1:2 to about 4:1.

In addition to the aforementioned components, the compositions of the present invention may also contain other pesticide adjuvants commonly employed in the art. Examples of such adjuvants include crop oil concentrate such as AGRIDEX® spreader such as ORTHO® X-77, drift control agents, such as LO-DRIFT®, defoaming agents, such as D-FOAMER®, compatibility agents, such as E-Z MIX®, and other adjuvants well known in the pesticide art. It is understood by those skilled in the art that the amount of these adjuvants in the pesticide composition can vary widely, and the amount needed can be readily determined by routine experimentation.

In order to prepare the pesticide compositions of the present invention, the pesticide active ingredient is combined at a level sufficient to deliver 0.025 to 1% volume/volume of surfactant blend to the tank mix upon dilution of the pesticide composition. For a given pesticide, the skilled artisan will readily arrive at a pesticidal composition having the optimum ratio of the ingredients by routine experimentation.

The above pesticidal composition may then be dispersed in water and sprayed onto plants according to the method of the present invention, described below. Alternatively, the surfactant blend of the present invention may be added directly to a water solution or dispersion of pesticide.

Whereas the scope of the present invention is set forth in the appended claims, the following specific examples illustrate certain aspects of the present invention. However, the examples are set forth for illustration only and are not to be construed as limiting on the present invention. All parts and percentages are by weight unless otherwise specified.

EXAMPLES

Polyalkyleneoxide polysiloxanes employed in the surfactant blends of the examples are set forth in Table 1.

TABLE 1

| Polyalkyleneoxide Polysiloxanes | |
|---|---|
| Polysiloxane | Structural Formula |
| | $(CH_3)_3SiO[SiO]_xSi(CH_3)_3$ with $CH_3$ and $R$ substituents |
| SILICONE 1 | $x = 1$ $R = C_3H_6O(C_2H_4O)_8CH_3$ |
| SILICONE 2 | $x = 1$ where $R = C_3H_6O(C_2H_4O)_8H$ |
| SILICONE 3 | $x = 1$ where $R = C_3H_6O(C_2H_4O)_8CCH_3$ with $=O$ |
| SILICONE 4 | $x = 1$ where $R = C_3H_6O(C_2H_4O)_{12}H$ |
| SILICONE 5 | $x = 1.2$ where $R = C_3H_6O(C_2H_4O)_6(C_3H_6O)_3H$ |
| SILICONE 6 | $x = 2$ where $R = C_3H_6O(C_2H_4O)_8CH_3$ |

Organic compounds employed in the surfactant blends of the examples are set forth in Table 2.

TABLE 2

| ID | Tradename Organic Compound | Chemical Type | Main Chain Hydrophobe | Average Moles Ethylene Oxide | CMC, %[1] | Surface Tension,[2] mN/M at 25° C. |
|---|---|---|---|---|---|---|
| 0-1 | Solvactant ® DMH-7 | Dimethylhexanol Ethoxylate | $C_6$ | 7 | 1.0 | 29.7 |
| 0-2 | Avirol ® SA-4106 | 2-Ethylhexyl Sulfate (Na) | $C_6$ | N/A | 1.7 | 51.4 |
| 0-3 | Dehydrol ® 04 | Octyl Alcohol Ethoxylate | $C_8$ | 4 | 0.25 | 34.1 |

TABLE 2-continued

| ID | Tradename Organic Compound | Chemical Type | Main Chain Hydrophobe | Average Moles Ethylene Oxide | CMC, %[1] | Surface Tension,[2] mN/M at 25° C. |
|---|---|---|---|---|---|---|
| O-4 | Triton ® CG, 110 | Alkyl Glucoside | $C_{8-10}$ | N/A | 0.05 | 27.6 |
| O-5 | Tergitol ® TMN-6 | Trimethylnonanol Ethoxylate | $C_9$ | 6 | N/A | — |
| O-6 | Tergitol ® TMN-10 | Trimethylnonanol Ethoxylate | $C_9$ | 10 | 0.096 | 28.5 |
| O-7 | Emulphogene ® DA-530 | Decyl Alcohol Ethoxylate | $C_{10}$ | 4 | 0.01 | 25.6 |
| O-8 | Emulphogene ® DA-630 | Decyl Alcohol Ethoxylate | $C_{10}$ | 6 | 0.01 | 26.8 |
| O-9 | Neodol ® 91-2.5 | Linear Alcohol Ethoxylate | $C_{9-11}$ | 2.5 | 0.006 | 25.8 |
| O-10 | Neodol ® 91-6 | Linear Alcohol Ethoxylate | $C_{9-11}$ | 6 | 0.008 | 27.4 |
| O-11 | Genapol ® 24-L-50[3] | Linear Alcohol Ethoxylate | $C_{12-14}$ | 7 | — | — |
| O-12 | Tergitol ® 15-S-5[3] | Secondary Alcohol Ethoxylate | $C_{11-15}$ | 5 | 0.002 | 28.1 |
| O-13 | Tergitol ® 15-S-7[3] | Secondary Alcohol Ethoxylate | $C_{11-15}$ | 7 | 0.004 | 29.6 |
| O-14 | Cationic (Lab Prep) | Dimethyloctylamine Acetate | $C_8$ | N/A | — | — |
| O-15 | Surfadone ® LP-100 | 1 Octyl-2-Pyrrolidione | $C_8$ | N/A | — | — |
| O-16 | Triton ® X-100[3] | Octylphenol Ethoxylate | N/A | 10 | — | 31.6 |

[1] CMC = Critical Micelle Concentration.
[2] Measured on aqueous solutions or dispersions at 0.1% w/w.
[3] These surfactants are included as comparative examples and are not part of the invention.

SPREADING. Solutions of surfactant blends used to measure spreading were prepared before each evaluation by one of two procedures.

(1) Two stock solutions each containing a single surfactant in deionized water which had been filtered through a Millipore® filtration system were combined immediately prior to testing; or (2) Two surfactants were blended together and formulated into a solution using deionized water which had been filtered through a Millipore® filtration system.

The influence of the organic compound on the spreading capability of the polysiloxane was determined by applying 10 μL of an aqueous solution containing the surfactant blend to a polyester film (3M IR 1174) using a microliter syringe. The spread diameter of the solution on the film was measured 30 seconds after its application at ambient conditions.

BIOLOGICAL EFFICACY. Surfactant blends were evaluated for efficacy as adjuvants, with pesticidal sprays according to the following procedure.

The weed test species were velvetleaf (Abutilon theophrasti) and morningglory (Ipomoea hederacea). All plants were established from seed. The plants were grown in a greenhouse for 14 days before treatments were applied.

The pesticide (REFLEX® from ICI, Wilmington, Del.) was prepared at 25% (0.0625 lbs/A) of the lowest label rate as recommended by the manufacturer. In addition, each of the surfactant blend/pesticide solutions were prepared to deliver a spray mixture containing 0.25% v/v of a surfactant blend, and a pesticide at a concentration to deliver 25% (0.0625 lbs/acre) of the lowest label rate recommended by the manufacturer. Pesticide treatments were applied at a rate of 20 gallons/acre, using an overhead track sprayer. Each of the treatments were done in triplicate using a randomized block design for placement in the greenhouse to minimize any effects resulting from location.

The use of the pesticide at a rate lower than recommended by the manufacturer enables the evaluator to observe the influence of the adjuvant on pesticide efficacy. Since the pesticide alone will have little or no effect on weed control at a rate lower than the manufacturer recommends, any improvement related to the adjuvant will become obvious.

Each weed species sprayed with a surfactant blend/pesticide solution was rated for weed control according to the following procedure. Untreated weed species were grown and after 14 days were cut off at the soil surface and weighed in order to obtain a fresh weight for the untreated weed species (FWU). Similarly, weed species treated with a surfactant blend/pesticide solution grown for the same 14 days were cut off at the soil surface and weighed in order to obtain a fresh weight for the treated weeds (FWT). The percentage amount of weed control was determined according to the equation:

$$\frac{FWU - FWT}{FWU} \times 100 = \% \text{ Weed Control}$$

EXAMPLE 1

Surfactant blends (50/50 and 75/25 organic compound to polysiloxane, respectively) using Silicone 1 and organic compounds containing hydrophobic moieties having differing numbers of carbon atoms in the main chain were prepared. The Spreading Index (SI) for 0.2 wt % of the surfactant blends were measured according the following equation:

$$SI (\%) = \frac{S^1 + S^2}{S^0} \times 100$$

where $S^1$ = spread value (diameter, mm) for 50/50 blend;

$S^2$ = spread value (diameter, mm) for 75/25 blend; and $S^0$ = cummulative spread value (diameter, mm) for the polysiloxane at a concentration equivalent to that found in 50/50 and in the 75/25 blend alone (i.e., without the organic compound).

When the SI is 50% or higher, the organic compound is considered to be less interfering than the Comparatives A, B, or C alone and spreading of the polysiloxane is considered to be acceptable. When the SI is less than 50% the organic compound is considered to exhibit a high degree of interference with the spreading of the polysiloxane.

The results are set forth in Table 3. From Table 3, it can be seen that organic compounds having a hydrophobic moiety having an average of 6 to 10 carbon atoms in main chain interfere less with the spreading of the organosilicone than organic compounds having a hydrophobic moiety with an average of eleven (11) carbon atoms or higher in the main chain.

TABLE 3

INFLUENCE OF HYDROPHOBIC MOIETY OF ORGANIC COMPOUND ON SPREAD OF SURFACTANT BLEND

| Run No. | Organic Compound | Number of Carbons in Hydrophobic Moiety | Spread Diameter, mm 50/50 Blend | Spread Diameter, mm 75/25 Blend | Spread Index (%) |
|---|---|---|---|---|---|
| Control[1] | none | N/A | 53 | 34 | N/A |
| 1 | O-1 | 6 | 48 | 38 | 99 |
| 2 | O-3 | 8 | 52 | 42 | 108 |
| 3 | O-5 | 9 | 41 | 15 | 64 |
| 4 | O-6 | 9 | 41 | 14 | 63 |
| 5 | O-7 | 10 | 41 | 27 | 78 |
| 6 | O-8 | 10 | 46 | 24 | 80 |
| 7 | O-9 | 9/11 | 31 | 27 | 67 |
| 8 | O-10 | 9/11 | 31 | 13 | 51 |
| A | O-11 | 12/14 | 14 | 10 | 28 |
| B | O-13 | 11/15 | 21 | 12 | 38 |
| C | O-16 | octyl phenol phenol | 12 | 10 | 25 |

[1] = Silicone 1 alone

In Table 3, in Run 1 the SI(%) is calculated as follows: $S^1=48$, $S^2=38$, $S^0=53+34$; therefore, $$\frac{S^1 + S^2}{S^0} = \frac{48 + 38}{53 + 34} \times 100$$

Surfactant blends (50/50 and 75/25) using Silicone 1 and organic compounds having a hydrophobic moiety of 6 to 10 carbon atoms and containing different hydrophilic moieties were prepared as in Example 1. The Spreading Index was measured as in Example 1. The results are set forth in Table 4.

Table 4 illustrates that the spreading index is favorable for surfactant blends in which the organic compound can contain a variety of hydrophilic moieties. That is, it is primarily the hydrophobic moiety that influences spreading.

TABLE 4

INFLUENCE OF HYDROPHILIC MOIETY OF ORGANIC COMPOUND ON SPREAD OF SURFACTANT BLEND

| Run No. | Organic Compound | Hydrophile | Hydrophobe | Number of Carbons in Hydrophobic Moiety | Spread Diameter mm 50/50 | Spread Diameter mm 75/25 | SI, % |
|---|---|---|---|---|---|---|---|
| Control[1] | None | Polyethylene-oxide | | N/A | 53 | 34 | N/A |
| 9 | O-2 | Sodium Sulfate | Anionic | 6 | 48 | 38 | 99 |
| 10 | O-3 | Polyethylene-oxide | Nonionic | 8 | 52 | 42 | 108 |
| 11 | O-4 | Polyglucoside | Nonionic | 8/10 | 41 | 15 | 64 |
| 12 | O-14 | Amine Acetate | Cationic | 8 | 41 | 27 | 78 |
| 13 | O-15 | Pyrrolidione | Nonionic | 8 | 34 | 15 | 56 |

[1]Control is Silicone 1 alone

EXAMPLE 3

Polysiloxanes, designated as Silicones 1 through 6 in Table 1 were blended (50/50) with organic compound O-3 of Table 2. Spreading was measured at 0.2 weight percent actives. The results are set forth in Table 5. The blends resulted in spreading performance similar to or better than those obtained when polysiloxane is used alone as observed by the SI, which was greater than 50 for each of polysiloxane structures.

TABLE 5

INFLUENCE OF DIFFERENT POLYSILOXANE STRUCTURES ON SPREAD OF SURFACTANT BLEND

| Run No. | Polysiloxane | Spread Diameter (mm) Polysiloxane Alone | Spread Diameter (mm) Blend (50/50) | SI* |
|---|---|---|---|---|
| 14 | Silicone 1 | 34 | 45 | 132 |
| 15 | Silicone 2 | 32 | 42 | 131 |
| 16 | Silicone 3 | 43 | 49 | 109 |
| 17 | Silicone 4 | 40 | 38 | 95 |
| 18 | Silicone 5 | 23 | 25 | 114 |
| 19 | Silicone 6 | 11 | 8 | 73 |

*SI = $S^1/S^0 \times 100$, where
$S^1$ = spread value (diameter, mm) for 50/50 blend and
$S^0$ = spread value (diameter, mm) for the polysiloxane at a concentration equivalent to that found in the 50/50 blends (0.1 wt %).

EXAMPLE 4

Crop oil concentrates as spray adjuvants were prepared using either mineral oil or methylated soybean oil as the carrier and the surfactant blend of the present invention. Spreading was evaluated by applying a 10 μL aqueous dispersion (2.0 wt %) of the crop oil concentrate to a polyester film with a microliter syringe. The spread diameter was measured after 5 minutes (i.e., maximum spreading for quick-drying dispersions). The results are set forth in Table 6.

The results illustrate that the surfactant blends of the present invention promote spreading of the dispersion of crop oil, and interfere less with spreading than surfactant blends containing a hydrophobic moiety having an average of 11 or more carbon atoms.

TABLE 6

INFLUENCE OF SURFACTANT BLENDS (50/50) ON THE
SPREADING OF CROP OIL CONCENTRATES

| RUN NO. | SURFACTANT BLEND | Crop Oil Concentrate[1], Wt % | | | NO. CARBONS IN HYDROPHOBIC MOIETY | SPREAD DIAMETER, mm |
|---|---|---|---|---|---|---|
| | | SURFACTANT BLEND | MINERAL OIL | METHYLATED SOYBEAN OIL | | |
| 20 | SILICONE 1+ 0-1 | 20 | 0 | 80 | 6 | 21 |
| 21 | SILICONE 1+ 0-3 | 20 | 0 | 80 | 8 | 24 |
| 22 | SILICONE 1+ 0-5 | 20 | 0 | 80 | 9 | 24 |
| 23 | SILICONE 2+ 0-7 | 20 | 0 | 80 | 10 | 28 |
| Control 1 | SILICONE 1+ 0-11 | 20 | 0 | 80 | 12–14 | 10 |
| 24 | SILICONE 1+ 0-1 | 20 | 80 | 0 | 6 | 36 |
| 25 | SILICONE 1+ 0-3 | 20 | 80 | 0 | 8 | 39 |
| 26 | SILICONE 1+ 0-5 | 20 | 80 | 0 | 9 | 10 |
| 27 | SILICONE 2+ 0-7 | 20 | 80 | 0 | 10 | 17 |
| Control 2 | SILICONE 1+ 0-11 | 20 | 80 | 0 | 12–14 | 7 |

[1]Evaluated as 2.0 wt. % aqueous dispersions or emulsions.

EXAMPLE 5

Morning glory and velvetleaf weeds were spray treated with REFLEX® (a diphenyl ether base herbicide) and the surfactant blend of the present invention. The results are set forth in Table 7. From Table 7, it can be seen that the pesticide in combination with the surfactant blends of the present invention was more effective than the pesticide alone in controlling weed growth.

TABLE 7

THE EFFECT OF SURFACTANT BLEND ON THE EFFICACY OF
PESTICIDE FOR THE CONTROL OF MORNINGGLORY AND VELVETLEAF

| RUN NO. | TREATMENT | | PERCENT WEED CONTROL | |
|---|---|---|---|---|
| | PESTICIDE[1] | BLEND | MORNINGGLORY | VELVETLEAF |
| D | REFLEX ® (0.0625 lb/A) | None | 40 | 3 |
| 28 | REFLEX ® (0.0625 lb/A) | Silicone 1 (0.125%) +0-1 (0.125%) | 80 | 67 |
| 29 | REFLEX ® (0.0625 lb/A) | Silicone 1 (0.125%) +0-3 (0.125%) | 76 | 68 |
| 30 | REFLEX ® (0.0625 lb/A) | Silicone 1 (0.125) +0-5 (0.125%) | 77 | 75 |
| 31 | REFLEX ® (0.0625 lb/A) | Silicone 2 (0.125%) +0-7 (0.125%) | 81 | 72 |
| | Control CHECK (i.e., without pesticide and Blend) | | 0 | 0 |

[1]Reflex ® at 0.0625 lb/$_A$ corresponds to only one-quarter (?) of the manufacturer's recommended use level to completely control these weed species.

EXAMPLE 6

Two surfactant blends, Emulsion 1 (consisting of Silicone 1 and 0-5 in a 1:1 ratio) and Comparative Emulsion 2 (Silicone 1 and PAO-20, a polyalkyleneoxide copolymer, in a 1:1 ratio) were used to emulsify light mineral oil (GLORIA® available from WITCO). The PAO and organic compound were chosen to have an HLB between 11.5 and 12.0. The HLB of the PAO was determined by comparing its cloud point with the cloud point of surfactants having known HLB values. The appropriate PAO used in this example contained approximately 20% by weight ethylene oxide (EO) and had a cloud point of approximately 32° C.

Emulsion 1 and Comparative Emulsion 2 were prepared by adding 4 grams of Silicone 1/0–5 or 4 grams of Silicone 1/PAO-20, respectively, along with 4 grams of distilled water to a 150-ml beaker. The components in each beaker were mixed for 1 minute with a shielded turbine blade at 500 rpms. Over a 10-minute interval, 20 grams of mineral oil were added to each beaker while mixing at 500 rpms continued. Distilled water (22 grams) was added to each beaker slowly over 10 minutes with mixing at 500 rpms. The resulting emulsions were placed in 4-ounce glass bottles and allowed to stand for 6 days. The stability of the two emulsions was assessed by the degree of separation after the six day period.

The results are set forth in Table 8. Table 8 demonstrates that Emulsion 1, the surfactant blend of the present invention, gave improved emulsification relative to a blend containing a silicone and a PAO (Comparative Emulsion 2).

TABLE 8

| INGREDIENT | EMULSION 1 | COMPARATIVE EMULSION 2 |
|---|---|---|
| O-5 | 2.0 g | 0 g |
| PAO-20 | 0 g | 2.0 g |
| SILICONE 1 | 2.0 g | 2.0 g |
| INITIAL WATER | 4.0 g | 4.0 g |
| MINERAL OIL | 20.0 g | 20.0 g |
| FINAL WATER | 22.0 g | 22.0 g |
| % STABILITY | 82 | 69 |

What is claimed is:

1. A surfactant blend comprising:

(a) 1 to 99% by weight of a polyalkyleneoxide polysiloxane having the general formula

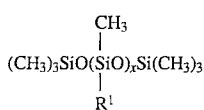

wherein x has a value of 1 or 2 and $R^1$ has the formula
—$C_nH_{2n}O(C_2H_4O)_a(C_3H_6O)_bR^2$
wherein n has a value of 3 or 4, a has a value of 1 to 15, b has a value of 0 to 14, a+b has a value of 5 to 15, and each $R^2$ is the same or different and is selected from the group consisting of hydrogen, an alkyl having 1 to 4 carbon atoms, and an acetyl group; and (b) 1 to 99% by weight of an organic compound having the general formula

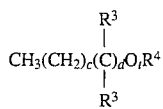

wherein $R^3$ is the same or different and is selected from the group consisting of hydrogen and an alkyl having 1 to 4 carbon atoms;

c has a value of 5 to 9, d has a value of 0 to 4, c+d has a value of 5 to 9, and t is 0 or 1

$R^4$ is a nonionic hydrophilic moiety with the proviso that when t is O, $R^4$ is

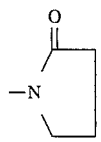

and when t is 1, $R^4$ is selected from the group consisting of (i) $[C_2H_4O]_f[C_3H_6O]_gH$ and (ii) $(C_6H_9O_5)_h$—$C_6H_{10}O_5$ wherein f has a value of 1 to 40, g has a value of 0 to 40, and h has a value of 1 to 4 wherein component (b) does not interfere with the spreading ability of component (a).

2. The surfactant blend according to claim 1 wherein X has a value of 1;

n has a value of 3;

a has a value of 6 to 9;

b has a value of 0 to 3;

a+b has a value of 6 to 9;

c has a value of 5 to 7;

d has a value of 0 to 3;

c+d has a value of 7 to 9;

f has a value of 2 to 15;

g has a value of 0 to 10.

3. The surfactant blend according to claim 1 wherein g has a value of 0.

4. The composition of claim 3 where the surfactant is an alkylpyrrolidone containing less than or equal to 8 carbons in the alkyl chain.

5. A surfactant blend comprising:

(a) 1 to 99% by weight of a polyalkyleneoxide polysiloxane having the general formula

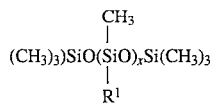

wherein x has a value of 1 or 2 and $R^1$ has the formula
—$C_nH_{2n}O(C_2H_4O)_a(C_3H_6O)_bR^2$
wherein n has a value of 3 or 4, a has a value of 1 to 15, b has a value of 0 to 14, a+b has a value of 5 to 15, and each $R^2$ is the same or different and is selected from the group consisting of hydrogen, an alkyl having 1 to 4 carbon atoms, and an acetyl group; and (b) 1 to 99% by weight of an organic compound having the general formula

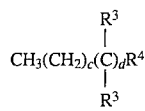

wherein $R^3$ is the same or different and is selected from the group consisting of hydrogen and an alkyl having 1 to 4 carbon atoms;

c has a value of 5 to 9, d has a value of 0 to 4, c+d has a value of 5 to 9, and $R^4$ is a cationic hydrophilic moiety selected from the group consisting of

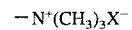  (i)

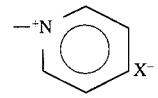  (ii)

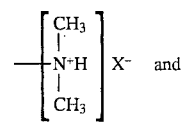  (iii)

and

-continued

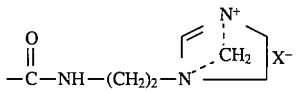 (iv)

wherein $X^-$ is selected from the group consisting of $Cl^-$, $Br^-$, $I^-$, $SO_4^-$, $HPO_4^-$, and $CH_3COO^-$.

6. The surfactant blend according to claim 5 wherein x has a value of 1,
n has a value of 3,
a has a value of 6 to 9,
b has a value of 0 to 3,
a+b has a value of 6 to 9,
c has a value of 7 to 9,
d has a value of 0 to 2,
c+d has a value of 7 to 9.

7. A surfactant blend comprising:
(a) 1 to 99% by weight of a polyalkyleneoxide polysiloxane having the general formula

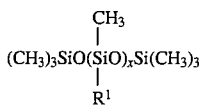

wherein x ]has a value of 1 or 2 and $R^1$ has the formula $-C_nH_{2n}O(C_2H_4O)_a(C_3H_6O)_bR^2$
wherein n has a value of 3 or 4,
a has a value of 1 to 15,
b has a value of 0 to 14,
a+b has a value of 5 to 15, and each $R^2$ is the same or different and is selected from the group consisting of hydrogen, and alkyl having 1 to 4 carbon atoms, an an acetyl group; and
(b) 1 to 99% by weight of an organic compound having the general formula

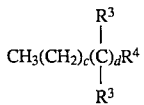

wherein $R^3$ is the same or different and is selected from the group consisting of hydrogen and an alkyl having 1 to 4 carbon atoms;
c has a value of 5 to 9,
d has a value of 0 to 4,
c+d has a value of 5 to 9, and
$R^4$ is a zwitterionic hydrophilic moiety selected from the group consisting of

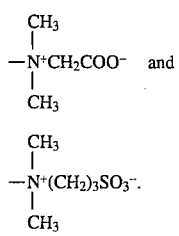

8. The surfactant blend according to claim 7 wherein x has a value of 1
n has a value of 3,
a has a value of 6 to 9,
b has a value of 0 to 3,
a+b has a value of 6 to 9,
c has a value of 7 to 9,
d has a value of 0 to 2,
c+d has a value of 7 to 9.

9. A surfactant blend comprising:
(a) 1 to 99% by weight of a polyalkyleneoxide polysiloxane having the general formula

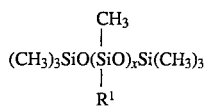

wherein x has a value of 1 or 2 and $R^1$ has the formula $-C_nH_{2n}O(C_2H_4O)a(C_3H_6O)_bR^2$
wherein n has a value of 3 or 4,
a has a value of 1 to 15,
b has a value of 0 to 14,
a+b has a value of 5 to 15, and each $R^2$ is the same or different and is selected from the group consisting of hydrogen, an alkyl having 1 to 4 carbon atoms, and an acetyl group; and
(b) 1 to 99% by weight of an organic compound having the general formula

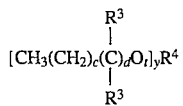

wherein $R^3$ is the same or different and is selected from the group consisting of hydrogen and an alkyl having 1 to 4 carbon atoms;
t is 0 or 1,
y is 1 or 2; and
$R^4$ is an anionic hydrophilic moiety with the provisos that
(1) when y is 1 and t is 1,
c has a value of 5 to 9,
d has a value of 0 to 4,
c+d has value of 5 to 9;
$R^4$ is selected from the group consisting of
(i) $-[C_2H_4O]_gSO_3^-M^+$ wherein g is 1 to 3 and
(ii) $-SO_3^-M^+$;
(2) when y is 1 and t is 0, then $R^4$ is $-SO_3^-M^+$ and
(3) when y is 2 and t is 1,
c has a value of 3 to 5,
d has a value of 0 to 2,
c+d is 4 or 5; and

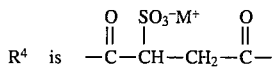

wherein $M^+$ is selected from the group consisting of $Na^+$, $Li^+$, $K^+$, $N(CH_3)_4^+$, and $[C_2H_4OH]_3NH^+$.

10. The surfactant blend according to claim 9 wherein
x has a value of 1,
n has a value of 3,
a has a value of 6 to 9,
b has a value of 0 to 3,
a+b has a value of 6 to 9,
with the provisos that when y is 1 and t is 1
c has a value of 7 to 9, d has a value of 0 to 2, c+d has a value of 7 to 9; and when y is 2 and t is 1 c is 5, d is 0, and c+d is 5.

11. A spreading composition comprised of at a 1:99 to 9:1 ratio by weight of an organosilicone surfactant and a alkylpolyglycoside comprised of 1 to 5 glucoside units in which the alkyl substituent contains less than 11 carbon atoms, wherein the organosilicone surfactant has the general structure:

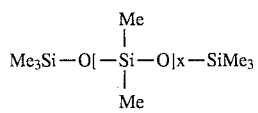

where $R^1 = C_n H_{2n} O (C_2 H_4 O)_a (C_3 H_6 O)_b R^2$;

$R^2$=H, an alkyl of 4 carbons or less or an acetyl group, n=3 to 4;

x=1 to 2;

a=1 to 15;

b=0 to 14; and a+b has a value of 5 to 15.

* * * * *